United States Patent
Westenfelder

(10) Patent No.: US 8,119,120 B2
(45) Date of Patent: Feb. 21, 2012

(54) MARROW STEM CELL AND PANCREATIC BETA CELL FUSION CELL USEFUL FOR THE TREATMENT OF DIABETES

(75) Inventor: Christof Westenfelder, Salt Lake City, UT (US)

(73) Assignee: Insugen, LLC, Salt Lake City, UT (US)

( * ) Notice: Subject to any disclaimer, the term of this patent is extended or adjusted under 35 U.S.C. 154(b) by 67 days.

(21) Appl. No.: 12/311,090

(22) PCT Filed: Sep. 19, 2007

(86) PCT No.: PCT/US2007/020359
§ 371 (c)(1),
(2), (4) Date: Sep. 15, 2009

(87) PCT Pub. No.: WO2008/036349
PCT Pub. Date: Mar. 27, 2008

(65) Prior Publication Data
US 2010/0034866 A1    Feb. 11, 2010

Related U.S. Application Data

(60) Provisional application No. 60/845,712, filed on Sep. 19, 2006.

(51) Int. Cl.
*C12N 15/00* (2006.01)
(52) U.S. Cl. .......... 424/93.2; 435/346; 435/449
(58) Field of Classification Search .......... None
See application file for complete search history.

(56) References Cited

U.S. PATENT DOCUMENTS

| | | | |
|---|---|---|---|
| 4,391,909 A | 7/1983 | Lim | |
| 6,881,555 B2 | 4/2005 | Guo et al. | |
| 2006/0084167 A1* | 4/2006 | Cohenford et al. | 435/325 |
| 2007/0178071 A1 | 8/2007 | Westenfelder | |

FOREIGN PATENT DOCUMENTS

WO   WO 2008/036349 A2   3/2008

OTHER PUBLICATIONS

Alvarez-Dolado et al. Fusion of bone-marrow-derived cells with Purkinje neurons, cardiomyocytes and hepatocytes. Nature, 2003, vol. 425, pp. 968-973.*
Chen et al.Differentiation of rat marrow mesenchymal stem cells into pancreatic islet beta-cells World Journal of Gastroent, 2004, vol. 10, 3016-3020.*
Tuttle et al.Regulation of pancreatic β-cell growth and survival by the serine/threonine protein kinase Akt1/PKBα Nature Med., 2001, vol. 7, pp. 1133-1137.*
Owen et al. Percutaneous Transhepatic Pancreatic Islet Cell Transplantation in Type 1 Diabetes Mellitus: Radiologic Aspects. Radiology, 2002, 229, pp. 165-170.*
Suzuki et al.Cyotomedical therapy for insulinopenic diabetes using microencapsulated pancreatic h cell lines Life Sciences, 2002, pp. 1717-1729.*
Jonas et al., Chronic hyperglycemia triggers loss of pancreatic beta cell differentiation in an animal model of diabetes, Journal of Biological Chemistry, May 14, 1999, pp. 14112-14121 [online], vol. 274, No. 20, [Retrieved on Feb. 18, 2008]. Retrieved from the internet: <URL:http://www.jbc.org/cgi/content/full/274/20/14112.
Shapiro et al., Islet Transplantation in Seven Patients with Type 1 Diabetes Mellitus Using a Glucocorticoid-Free Immunosuppressive Regimne, New England Journal of Medicine, Jul. 27, 2000, pp. 230-238, [online] vol. 373, No. 4, [Retrieved on Feb. 18, 2008]. Retrieved from the internet: <URL: https://content.nejm.org/cgi/reprint/343/4/230.pdf.
EMEA, European Agency for the Evaluation of Medical Products, "Points to Consider on Xenogenic Cell Therapy Medicinal Products," Dec. 17, 2003, p. 17 [online]. Retrieved on http://www.emea,europa,eu/pdfs/human.cpwp/119902en.pdf.
Supplementary Partial European Search Report, EP 07 86 1344, dated Nov. 27, 2009.
Islam et al., Abstract, Functional characterization of cell hybrids generated by induced fusion of primary porcine mesenchymal stem cells with an immortal murine cell line, Cell and Tissue Research, Jun. 2, 2006, pp. 123-137, vol. 326, No. 1.
Garbade et al., Abstract, Fusion of bone marrow-derived stem cells with cardiomyocytes in a heterologous in vitro model, European Journal of Cardio-Thoracic Surgery, Nov. 1, 2005, pp. 685-691, vol. 28, No. 5, Springer Verlag, Berlin, DE.
He et al., Abstract, A stem cell fusion model of carcinogenesis, Journal of Experimental Therapeutics and Oncology, Jan. 1, 2005, pp. 101-109, vol. 5, No. 2, Rapid Science Publishers, London, GB.
Yoshida et al., Abstract, TPA-induced multinucleation of a mesenchymal stem cell-like clone is mediated primarily by karyokinesis without cytokinesis, although cell-cell fusion also occurs, European Journal of Cell Biology, Jul. 29, 2007, pp. 461-471, vol. 86, No. 8, Wissenschaftliche Verlagsgesellschaft, Stuttgart, DE.
PCT International Preliminary Report on Patentability, PCT/US2007/020359, dated Apr. 2, 2009.
Cowan et al., Nuclear Reprogramming of Somatic Cells After Fusion with Human Embryonic Stem Cells, Science, 2005, pp. 1369-1373, vol. 309.
Kemp et al., Fusion between human mesenchymal stem cells and rodent cerebellar Purkinje cells, Neuropathology and Applied Neurobiology, 2011, pp. 166-168, vol. 37.
Le Blanc, Mesenchymal stromal cells: tissue repair and immune modulation, Cytotherapy, 2006, pp. 559-561, vol. 8, No. 6.
Lee et al., Multipotent stromal cells from human marrow home to and promote repair of pancreatic islets and renal glomeruli in diabetic NOD/scid mice, PNAS, Nov. 14, 2006, pp. 17438-17443, vol. 103, No. 46.
Li et al., Electrofusion between Heterogeneous-Sized Mammalian Cells in a Pellet: Potential Applications in Drug Delivery and Hybridoma Formation, Biophysical Journal, Jul. 1996, pp. 479-486, vol. 71.
Lluis et al., Embryonic Stem Cells/Induced Pluripotent Stem Cells, Stem Cells, 2010, pp. 1940-1949, vol. 28.
Ogle et al., Biological implications of Cell Fusion, Nature Reviews, Molecular Cell Biology, Jun. 2005, pp. 567-575, vol. 6.

(Continued)

*Primary Examiner* — Deborah Crouch
(74) *Attorney, Agent, or Firm* — TraskBritt

(57) ABSTRACT

Methods disclosed include methods of treating T1DM, said method comprising delivering a therapeutic amount of β-MSC to a subject in need thereof. Further disclosed are fusion cells comprising and MSC and a second cell wherein the nuclei of the MSC and the second cell are not fused in the fusion cell.

14 Claims, 5 Drawing Sheets

OTHER PUBLICATIONS

Palermo et al., Nuclear reprogramming in heterokaryons is rapid, extensive and bidirectional, The FASEB Journal, May 2009, pp. 1431-1440, vol. 23.

Pomerantz et al., Reprogramming to a muscle fate by fusion recapitulates differentiation, Journal of Cell Science, 2008, pp. 1045-1053, vol. 122.

Shi et al., Myogenic fusion of human bone marrow stromal cells, but not hematopoietic cells, Blood, 2004, pp. 290-294, vol. 104.

Singec et al., Inflammation as a matchmaker: revisiting cell fusion, Nature Cell Biology, May 2008, pp. 503-505, vol. 10, No. 5.

Sukhorukov et al., Surviving High-Intensity Field Pulses: Strategies for Improving Robustness and Performance of Electrotransfection and Electrofusion, J. Membrane Biol., 2006, pp. 187-201, vol. 206.

Togel et al., Adult Bone Marrow—Derived Stem Cells or Organ Regeneration and Repair, Developmental Dynamics, 2007, pp. 3321-3331, vol. 236.

* cited by examiner

MARROW STEM CELL AND PANCREATIC BETA CELL FUSION CELL USEFUL FOR THE TREATMENT OF DIABETES

PRIORITY CLAIM

This application claims the benefit of the filing date of U.S. Provisional Patent Application Ser. No. 60/845,712, filed Sep. 19, 2006, for "NOVEL STEM CELL AND USES THEREOF FOR SUBJECTS WITH INSULIN-DEPENDENT DIABETES MELLITUS," the contents of each of which are incorporated herein by this reference.

TECHNICAL FIELD

The present invention generally relates to the fields of biotechnology and therapies using bone marrow-derived stem cells fused with cells. In one example, insulin-dependent diabetes mellitus may be treated by a fusion cell made from marrow-derived stem cells fused to pancreatic β cells.

BACKGROUND

The prevalence of diabetes mellitus (DM) has increased world wide from 30 million in 1985 to 180 million currently, and is predicted to rise to 366 million by the year 2025. In developing countries such as China and India, the number of cases diagnosed with new onset DM is increasing at a stunning rate of 3,000 per day. And currently more than 1 in 400 children become insulin dependent due to Type 1 DM (T1DM), due to autoimmune-mediated destruction of pancreatic β cells. In 2003 in the USA there were 14.6 million individuals with the diagnosis of DM. 7% or 1.02 million of which were subjects with T1DM (Diabetes Atlas 2003). Despite treatment, often futile, with exercise, weight control, and oral agents, the vast majority of subjects with adult onset, Type 2 DM (T2DM), characterized by primary insulin resistance, will eventually become insulin dependent because of pancreatic β cell failure. This is associated with advanced manifestations of the diabetic state, such as retinopathy, neuropathy, nephropathy, and major cardiovascular and infectious complications, collectively resulting in ever increasing medical expenses, morbidity and mortality rates. In 2003 in Europe, a total of 48.4 million subjects were diagnosed with DM, and 7% of these or 3.5 million were subjects with T1DM. However, despite the life-sustaining actions of insulin injections in affected individuals by preventing diabetic ketoacidosis, exogenous insulin does not protect against secondary micro- and macro-vascular complications such as diabetic retinopathy (blindness), nephropathy (renal failure, dialysis dependency, need for kidney transplant), stroke, neuropathy, limb amputations, coronary artery disease with myocardial infarction, and congestive heart failure. The resulting shortened life span in affected subjects demonstrates that injected insulin is a suboptimal form of therapy. Currently, more optimal therapies to replace endogenous insulin in subjects with T1DM include glucose-responsive, closed-loop insulin pumps, whole pancreas transplants, often combined with a kidney transplant, or a pancreatic β cell or islet transplant. Both forms of transplant depend on the availability of suitable cadaveric donors. To date, approximately 1,200 subjects world wide have been treated with islet transplants, while more than 75,000 received whole pancreas grafts. The following challenges with these forms of therapy continue to limit the urgently needed, large scale establishment of these promising interventions: (i) the availability of sufficient cadaveric pancreas/islet donors is grossly inadequate, (ii) this scarcity is further aggravated because frequently two pancreas donors are needed in order to generate sufficient islet numbers for one recipient, (iii) since the ability to culture expand pancreatic islets in vitro is small, an appropriate β cell supply for subjects in need thereof is currently not available, (iv) islet survival in the portal vein, the site of islet transplantation, is limited due to immune and non-immune injuries, resulting in progressive return of partial or complete insulin dependency after one to five years, (v) the need for lifelong immunosuppressant drugs, to prevent rejection, in graft recipients is associated with major adverse effects such as serious infections, malignancies, and kidney failure.

Taken together, despite encouraging progress with islet and pancreas transplantation, these highly desirable forms of endogenous, physiologically regulated insulin replacement are hampered by the above challenges and have thus far provided successful therapy for only a very small fraction of subjects with T1DM. Islet or pancreas transplantation for improvement in the quality of life of subjects with insulin-dependent T2DM has not been considered because the primary defect in these is peripheral insulin resistance with secondary β cell failure. Thus, unless insulin resistance in these subjects can be eliminated, exhaustion of transplanted β cell and subsequent β cell failure will destroy the islet cell grafts, while exposing the subject to the high risks of immunosuppressive drugs.

Very promising pre-clinical in vitro and animal studies and a few early phase clinical trials have demonstrated that pluripotent Mesenchymal Stem Cells or Marrow Stromal Cells (MSC) possess immunomodulating capabilities by inhibiting the T-cell or rejection response. MSC can be readily harvested from the bone marrow of a donor (allogeneic source) or a subject (autologous source), expanded in culture, differentiated into cells of mesodermal and non-mesodermal phenotype, cryopreserved, and administered for organ repair (e.g., kidney, heart, spinal cord, brain, or bone), as adjuvant to a bone marrow transplant with hematopoietic stem cells (HSC), for the treatment of grade IV Graft versus Host Disease, osteogenesis imperfecta, Hurler's syndrome, and other indications. Long term studies have shown that MSC do not undergo malignant transformation, a concern that potentially affects embryonic stem cell therapies. And, the utilization of these cells is not afflicted by ethical concerns.

In conclusion, a need exists for the development and clinical testing and introduction of fundamentally novel therapies for subjects with T1DM. Cell based new technologies that successfully address the challenges and obstacles that are currently encountered with islet cell transplantation (see above) are expected to dramatically increase the number of diabetic subjects that can receive long lasting replacement of endogenous insulin.

DISCLOSURE OF INVENTION

The present invention may utilize MSC and pancreatic β cells for the treatment of T1DM. In one aspect of the invention, allogeneic or autologous MSC may be harvested from a donor or T1DM subject, respectively, by, in a non-limiting example, aspiration of 50 cc whole bone marrow from the posterior iliac crest under local anesthesia. MSC for administration may be derived from bone marrow cells that are placed into sterile culture in vitro. Except for MSC, practically all other cells contained in a bone marrow aspirate will not adhere to the bottom of a culture dish (Friedenstein, *Exp. Hematol.* 4:267-74, 1976). After discarding the non-attached cells, MSC may be grown and expanded in culture, to yield a well defined population of pluripotent stem cells, capable of canonical mesenchymal differentiation into fat, bone, and cartilage cells. After expansion in vitro, collected MSC may be further depleted of CD 45 positive cells, by FACS, in order to remove residual macrophages or other hematopoietic cell lineages prior to further processing. MSC may be derived from the subject or, under defined circumstances, from a compatible donor. Donor stem cells may be used from a donor having similar compatibility as defined for the organ to be transplanted, known to one skilled in the art, although the inherent immunomodulating capacity of MSC may render this step unnecessary. As MSC may be readily expanded in vitro, a treatment regime with MSC may be easily repeated and/or augmented, for example, in order to further provide an optimal number of cells. Any method known to one of skill in the art may be used to enrich a population of pluripotent MSC from a whole population of bone marrow cells, and, if desired, cryopreserve them for future use.

In embodiments of the invention, MSC may be isolated from any source. Examples of sources of MSC include but are not limited to, isogenic, syngeneic, xenogenic, and/or mammalian sources. Examples of mammalian sources include, but are not limited to, humans, pigs, mice, rats, dogs, cows, sheep, cats, horses, monkeys, etc. In embodiments of the invention, the source of MSC may be allogenic to the recipient, irrespective of species.

First cells for fusion with MSC may be obtained from any source. In embodiments of the invention, the source of cells for fusion is an isogenic, allogenic, syngeneic, xenogenic, and/or mammalian source. Examples of mammalian sources include, but are not limited to, humans, pigs, mice, rats, dogs, cows, sheep, cats, horses, monkeys, etc. In embodiments of the invention, the source of cells to be fused with MSC may be allogenic to the recipient, irrespective of species. As will be apparent to one of ordinary skill in the art, the type of cell selected from the source will depend on the disease and/or condition to be treated with fusion cells. Types of cells include, but are not limited to, totipotent stem, pluripotent stem, multipotent stem, progenitor, liver, heart, marrow, bone, central nervous system, peripheral nervous system, immune, skin, eye, lung, kidney, gastrointestinal, and muscle cells. Types of conditions and/or diseases to be treated may include, but are not limited to conditions and diseases involving the foregoing exemplary list of cells.

In one embodiment of the invention, pancreatic β cells may be derived, for example, from the pancreas of a cadaveric donor, potentially from a pancreas segment of a living donor, using islet isolation and cell dispersion methods known to one of ordinary skill in the art. Viable pancreatic β cells may be placed in short term culture and once stable, MSC may be added for co-culture. In embodiments, the MSC may be added in, by way of non-limiting examples, 1:1, 1:2, 1:3 and higher, defined ratios. A ~50% fraction of MSC and pancreatic β cells may be induced and spontaneously undergo cellular, not nuclear fusion, resulting in chimeric β-MSC. The resultant heavier chimeric β-MSC may be isolated and returned to routine culture, in which they readily proliferate and maintain their phenotype, characterized by double nuclei (one from the original MSC, one from the pancreatic β cell). Examples of methods of isolation include, but are not limited to, Ficoll gradient centrifugation and FACS. β-MSC produce and secrete authentic insulin into the media when, ambient glucose levels are raised, for example, step-wise from 0 to 750 mg, showing a dose response relationship. Insulin synthesis and secretion may diminish and fall to zero as ambient glucose concentrations are gradually lowered to less than 100 mg/dL. The viability of β-MSC is not affected by changes in media glucose concentration, as long as changes are made gradually, allowing cellular adaptation. Native MSC do not synthesize or secrete insulin as media glucose concentrations are altered. Cellular "fusion" physiologically exists in skeletal and cardiac muscles, as well as in the liver. In addition, it has been reported that administered stem cells undergo fusion with intestinal stem cells, and several reports have emphasized that administered stem cells can fuse with target cells of injured organs such as the liver, CNS and heart. There is currently no evidence that fusion of MSC with differentiated cells, such as pancreatic β cells, results in malignant transformation or cellular instability.

In embodiments of the invention, the compositions of invention may be administered to a subject. Subject, as used herein, refers to any organism that it may be beneficial to administer one or more of said compositions to. In embodiments, the subject may be one in need of treatment via administration of one or more of said compositions. Examples of subjects include, but are not limited to, mammals, humans, pigs, mice, rats, dogs, cows, sheep, cats, horses, monkeys, etc.

Subjects with T1DM may be treated with sufficient β-MSC to achieve complete or partial replacement of endogenous insulin, resulting in avoidance or attenuation of one or both of hypo- and hyperglycemia, as well as diabetic ketoacidosis. Blood C-peptide, insulin, and/or glucose levels may be monitored top assess functionality of cells and to determine whether additional cells may be needed. Since insulin secretion by β-MSC is physiologically responsive to ambient glucose levels, hypoglycemia is less likely than hyperglycemia. The latter, if it persists, might be used as an indication that additional β-MSC are needed. β-MSC may be administered by way of non-limiting examples, either into the portal vein with a catheter, as is routinely done with islet transplant, or may be placed into a porous, plastic capsule that permits access of glucose and release of insulin. Such a capsule may be, for example, placed into the anterior abdominal wall, only covered by the peritoneum, allowing easy replacement and removal. Functionality of administered β-MSC may be monitored by measurement of blood C-peptide, insulin, and/or glucose levels. As may be needed over time, subjects may be provided with additional β-MSC.

Allogeneic β-MSC, derived from a compatible MSC donor, may also be used for administration. Reasons for administering allogeneic MSC might include: (a) the bone marrow in a T1DM subject who is found to need β-MSC therapy may be a poor source of adequate numbers of MSC because of the underlying diabetic state; (b) a subject may refuse or may not be able to consent to the harvesting of his/her own bone marrow cells; (c) the bone marrow-derived stem cells from a compatible living-related or unrelated donor of a solid organ may be of superior quality and quantity compared to the recipient's own stem cells.

"Treating," "treatment," or "therapeutically effective dose" does not require a complete cure. It means that the symptoms of the underlying disease or condition are at least reduced, and/or that one or more of the underlying cellular, physiological, or biochemical causes or mechanisms causing the symptoms or phenotype are reduced and/or eliminated. It is understood that reduced, as used in this context, means relative to the state of the disease or condition, including the molecular state of the disease or condition, not just the physiological state of the disease or condition.

In certain embodiments, a therapeutically effective dose of β-MSC may be delivered to the subject. An effective dose for treatment may be determined by the body weight of the subject receiving treatment, by his/her current insulin requirements (short and long acting insulin), and/or may be further modified based on the duration of T1DM, and/or the simultaneous presence or absence of comorbidities that alter insulin requirements, such as kidney or liver diseases. A therapeutic dose may comprise one or more administrations of the therapy.

If β-MSC survival and function in a recipient is found to be inadequate/too short, a next population of β-MSC may engineered so as to enhance β-MSC survival. One non-limiting example of such engineering may be preformed by viral transfection to induce or otherwise provide for the over expressions of Akt, a gene product that is essential to pancreatic β cell function and is well known to greatly enhance MSC survival via its anti-apoptotic actions. Serendipitously, MSC produce VEGF, a potent vasculo-supportive cytokine, HGF and IGF-I, a survival factors in solid organs, and possess powerful anti-inflammatory activity, which together or separately may result in the delivery, intraportal or otherwise, of beneficial cytokines and survival factors.

Several methods may be used to monitor the cellular fusion of mouse MSC with mouse pancreatic β cells. In one non-limiting example, MSC were labeled with a green fluorescent vital dye, while isolated β cells were labeled with a red fluorescent vital dye. These vital dyes, i.e., dyes that have no harmful effect on living cells, allow the precise assessment of cell fusion, using techniques commonly known in the art. A further non-limiting method used to monitor cell fusion utilized Fluorescent In Situ Hybridization (FISH assay) for the male "Y" chromosome, using MSC from male mice and β cells from female mice. In further embodiments, fused cells may be isolated from non-fused cells by any suitable method. Examples of suitable methods include, but are not limited to, cell weight and/or DNA content. Since fused cells are heavier than native cells, they may be separated by Ficoll gradient centrifugation, using standard methodology. The higher DNA content of fused cells allows their isolation by FACS. RT-PCR, Western blots, and immunocytochemistry are additional methods that may be used to confirm fusion of pancreatic β cells with MSC. Identifying characteristic gene expression profiles and cytosolic and cell surface protein expression may also be used. Fusion of mouse MSC from one strain of mice (FVB/JN) with mouse pancreatic β cells from another strain of mice (Swiss Black) resulted in allogeneic β-MSC, exhibiting comparable characteristics (proliferation, physiological insulin secretion) with those obtained by isogeneic fusion of both cell types. Additionally, fusion of rat MSC with mouse pancreatic β cells resulted in xenogeneic β-MSC, also exhibiting comparable characteristics (proliferation, physiological insulin secretion) with those obtained by isogeneic fusion of both cell types.

In another aspect of the present invention, the above delineated technologies may be established in primary, secondary, and/or tertiary care centers world wide. Multidisciplinary "Cell Therapy Teams" could be owned and operated by international Health Care Equipment and Service companies that may also produce and sell their or other companies' kits and materials used for the harvesting, purification, culturing, fusion, engineering, cryopreservation and administration of β-MSC and/or other MSC fusions. Physicians (for example, internists, endocrinologists, transplant surgeons, intensivists, etc.) who may care for a group of subjects who would benefit from MSC fusion based therapy would order respective cell-based services, and these specialized teams would provide the requested treatment.

In certain embodiments of the present invention, the MSC utilized for these treatments may be "harvested" and prepared on site, i.e., in a hospital by a specialized team from, for example, the following donors: 1) a subject will donate his/her own bone marrow to obtain MSC for treatment of his/her own T1DM, i.e., autologous stem cells, while pancreatic β cells will be obtained from a cadaveric, allogeneic donor. 2) A living related or un-related, allogeneic or xenogenic donor may provide MSC and/or β cells derived from a donated segment of the pancreas. 3) In some cases, the subject's own pancreas may provide sufficient starter β cells that can be fused and expanded in culture with his/her own MSC or those of a live donor.

Provided is a novel cell therapy that successfully addresses the major obstacles that islet transplantation in subjects with T1DM faces: (i) since β-MSC proliferate in culture while maintaining their phenotype (physiological secretion of insulin), this technique allows for the production of sufficient cells for single or repeated dosing in a given subject or multiple subjects, using either autologous or allogeneic protocols; (ii) β-MSC survival in the portal vein or in an abdominally implanted, porous capsule, is expected to be prolonged because of the immunomodulating capacity of MSC (reduces immune injury), and because of the beneficial cytokines that MSC release (HGF, VEGF, IGF-I and others), and, if necessary, survival can be further prolonged, for example, by prior transfection with Akt. Furthermore, additional cells may be administered as needed (cryopreserved and stored in a GMP Cell Bank), (iii) the need for life long immunosuppressant drugs, to prevent rejection, in graft recipients may avoided or attenuated because of the immunomodulating activity of MSC.

Further provided are uses of a cell fusion of a first cell and an MSC for the treatment of a condition or a disease. In particular embodiments, the condition or disease may be diabetes, type 1 diabetes, or type 2 diabetes.

Embodiments include pharmaceutical compositions and/or medicaments comprising the cell fusion of an MSC and a first cell. Embodiments of a pharmaceutical composition may also comprise a pharmaceutically acceptable excipient. Examples of pharmaceutically acceptable excipient include, but are not limited to, sterile water, phosphate buffered saline, saline, ringer's solution, and those provided in REMINGTON'S PHARMACEUTICAL SCIENCES, 18th Ed. (1990, Mack Publishing Co., Easton, Pa.) and GOODMAN AND GILMAN'S, THE PHARMACOLOGICAL BASIS OF THERAPEUTICS ($10^{th}$ ed. 2001). Embodiments include pharmaceutical compositions and/or medicaments comprising the cell fusion of an MSC and a pancreatic β cell.

Embodiments include the use of a cell fusion of an MSC and a first cell in the manufacture of a medicament. In additional embodiments, the medicament may be useful for the treatment of diabetes mellitus. Certain embodiments include the use of a cell fusion of an MSC and a pancreatic β cell in the manufacture of a medicament for the treatment of diabetes mellitus.

MODES FOR CARRYING OUT THE INVENTION

The present invention is further described in the following examples, which are offered by way of illustration and are not intended to limit the invention in any manner.

EXAMPLE 1

Protocol for Isolation and Fusion of PβC with MSC: Generation of β-MSC

Isolation of islets from male mouse pancreata was performed as follows: mouse pancreata were treated with collagenase XI; the resulting cells were separated from debris via a ficoll gradient; live cells were hand picked and plated. Cells were later stained to confirm presence of PβC.

PβC were isolated from the islet cell culture via exposing the above cultures to trypsin-EDTA for 3 minutes and removing the cells that were no longer adherent.

Syngeneic female MSC (immortal) were grown from mouse bone marrow using techniques for MSC isolation known in the art.

EXAMPLE 2

Determine the Ratio of MSC and Pancreatic β Cells (PβC) for Optimal Cellular Fusion Starting with a 1:1 ratio of co-cultured isogeneic MSC and isolated PβC from mice ~50% of cells were fused (PβC fused with MSC) as confirmed by the use of distinct vital dyes for each cell type, by FISH for the "Y" chromosome (male-derived MSC, female-derived PβC), RT-PCR, Westerns, and immunocytochemistry. In addition, Ficoll gradient centrifugation and FACS analysis corroborated the extent of cell fusion accomplished in co-culture. In additional studies, initial cell ratios in co-culture will be varied (up and down) in order to assess whether the extent of cell fusion can be further optimized.

Figure 1:
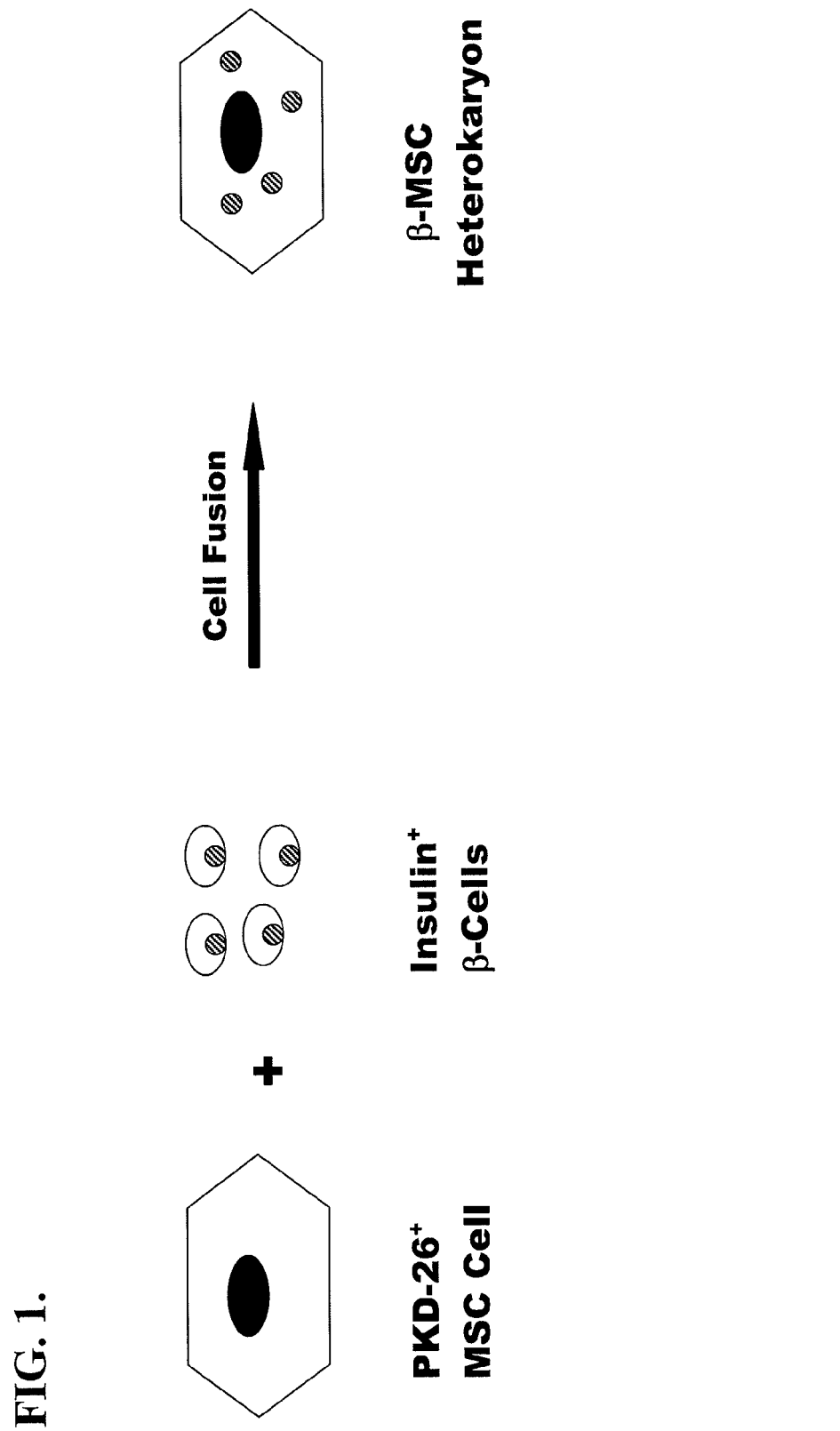
FIG. 1 schematically shows the fusion of an MSC (staining for Protein Kinase D-26 (PKD-26), a cell surface marker for MSCs) and a PβC (staining for insulin) into a β-MSC hybrid cell (staining for both PKD-26 and insulin).

PβC and MSC were co-cultured at ratios of 1:1 and 2:1. Fusion was induced by phytohemagglutinin and by changing the medium to polyethylene glycol (45% w/v) for 1 minute and then washing. Cells were then cultured for 24 hours before being removed by treatment with trypsin-EDTA and replated. Hybrid colonies were formed within 5-7 days. FIG. 1 schematically shows the fusion of an MSC (staining for Protein Kinase D-26 (PKD-26), a cell surface marker for MSCs) and a PβC (staining for insulin) into a β-MSC hybrid cell (staining for both PKD-26 and insulin).

EXAMPLE 3

Determine the Ability of β-MSC to Physiologically Release Insulin in Culture

Freshly fused β-MSC that were not passaged in culture were isolated by FACS or Ficoll gradient centrifugation. β-MSC express insulin by RT-PCR and ELISA (secretion into media). Glucose concentrations in serum free media were adjusted to 0 and gradually raised to 50, 100, 250, 500 and 750 mg/dL (45 minutes at each concentration). Media concentrations of insulin and C-Peptide were determined at the end of each 45-minute period by sensitive ELISA assays, showing a glucose level-dependent rise of both. Cells adapted to 750 mg/dL of media glucose were then exposed to the reverse pattern of glucose concentrations in the media, showing a step wise fall in insulin and C-Peptide levels. Native MSC do not secrete insulin or C-Peptide, while PβC per se respond to changes in ambient glucose levels in a pattern identical to that of fused cells.

Figure 2:
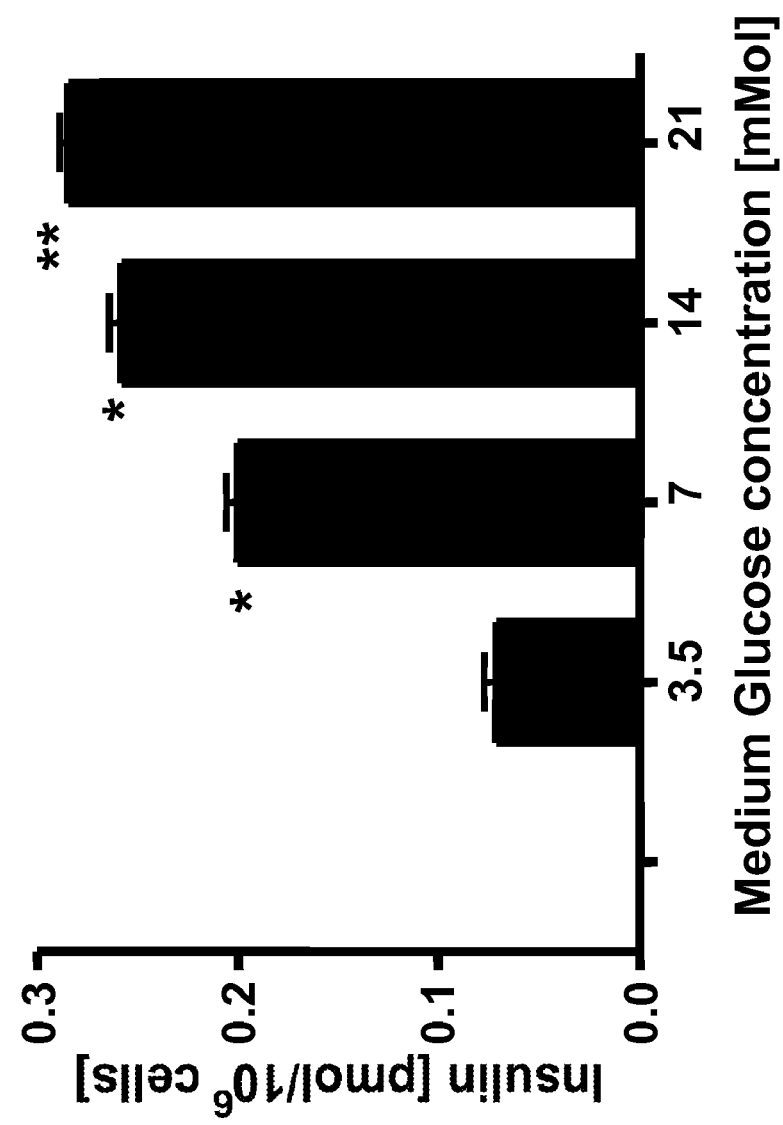
FIG. 2 depicts insulin release in pmol/$10^6$ cells from β-MSC treated with glucose containing medium in concentrations ranging from 3.5 to 21 mMol glucose. * indicates $P<0.001$ while ** indicates $P<0.05$.
Figure 3:
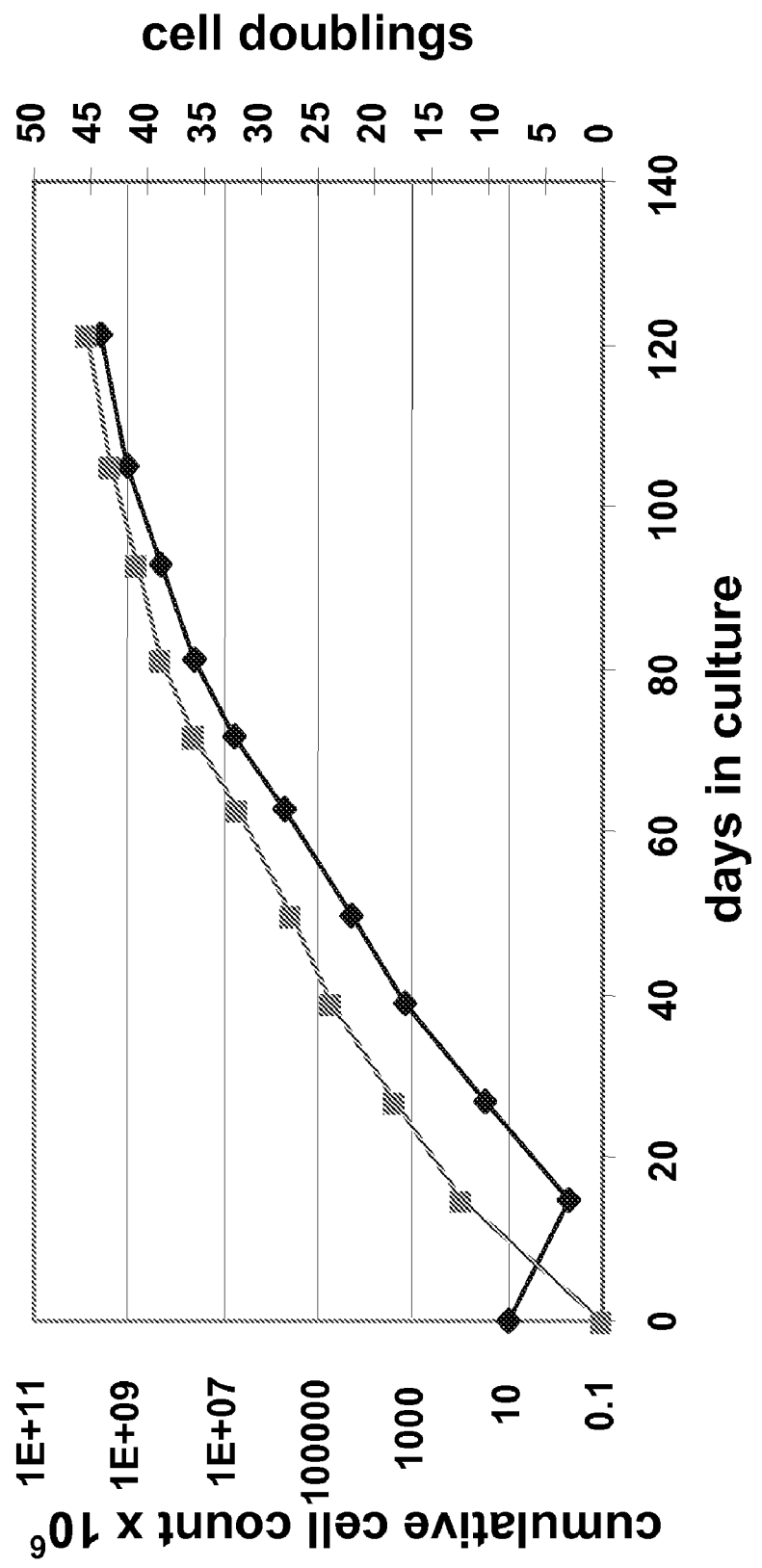
FIG. 3 depicts the growth kinetics of β-MSC cells during expansion in medium comprising fetal calf serum. The cumulative cell count is indicated by the trace marked with diamonds while the number of cell doublings is indicated by the trace marked with squares.

FIG. 2 depicts insulin release from β-MSC treated with glucose containing medium. As can be seen therein, insulin production levels increase with the intensity of the glucose challenge.

EXAMPLE 4

Determine whether β-MSC Proliferate and Maintain their Phenotype

Freshly fused β-MSC were placed in standard culture flasks (T25) with DMEM/F12 media, 10% FCS, incubated at pH 7.40, 37° C., with 5% $CO_2$ and room air. Cells were passaged on day 3 when ~75% confluent. After ten passages, cells were analyzed for fusion status (as in Example 1), and for their ability to secrete insulin and C-Peptide in response to changes in ambient glucose concentration (as in Example 2). ~80% of cells retained their phenotype (fused) and these cells exhibited physiological insulin and C-Peptide secretion patterns analogous to those obtained in freshly fused, P0 cells.

β-MSC isolated as in Example 2 where grown in culture medium containing 10% fetal calf serum for 120 days under the conditions indicated above. As is shown in FIG. 2, β-MSC underwent 45 doublings over then 120 period producing more than $10^{14}$ cells.

EXAMPLE 5

Determine Whether Intraperitoneal Administration of β-MSC to Diabetic Mice Improves Glucose Control Six months old db/db mice develop hyperglycemia and show early systemic manifestations of DM (proteinuria, hypertension, dyslipidemia). Three groups (n=6) of animals were studied: 1) controls, not given β-MSC but 0.2 ml of PBS as vehicle; 2) β-MSC ($1.5 \times 10^5$; syngeneic wild type) infused in 0.2 ml PBS into the peritoneal cavity; 3) native MSC ($1.5 \times 10^5$; syngeneic wild type) infused in 0.2 ml PBS into the peritoneal cavity. Animals were followed for four weeks. Blood microsamples were assayed for glucose every other day, and serum insulin, C-Peptide and glucose levels were determined once every seven days. We observed identical hyperglycemic levels (250±50 mg/dL average) in group 1) control and group 3) native MSC groups, while group 2) β-MSC animals had blood sugar levels between 85±12 and 120±15 mg/dL (±SD). Only group 2) animals gained weight and serum insulin and C-Peptide levels showed a physiological correlation with blood sugar levels.

Figure 4:
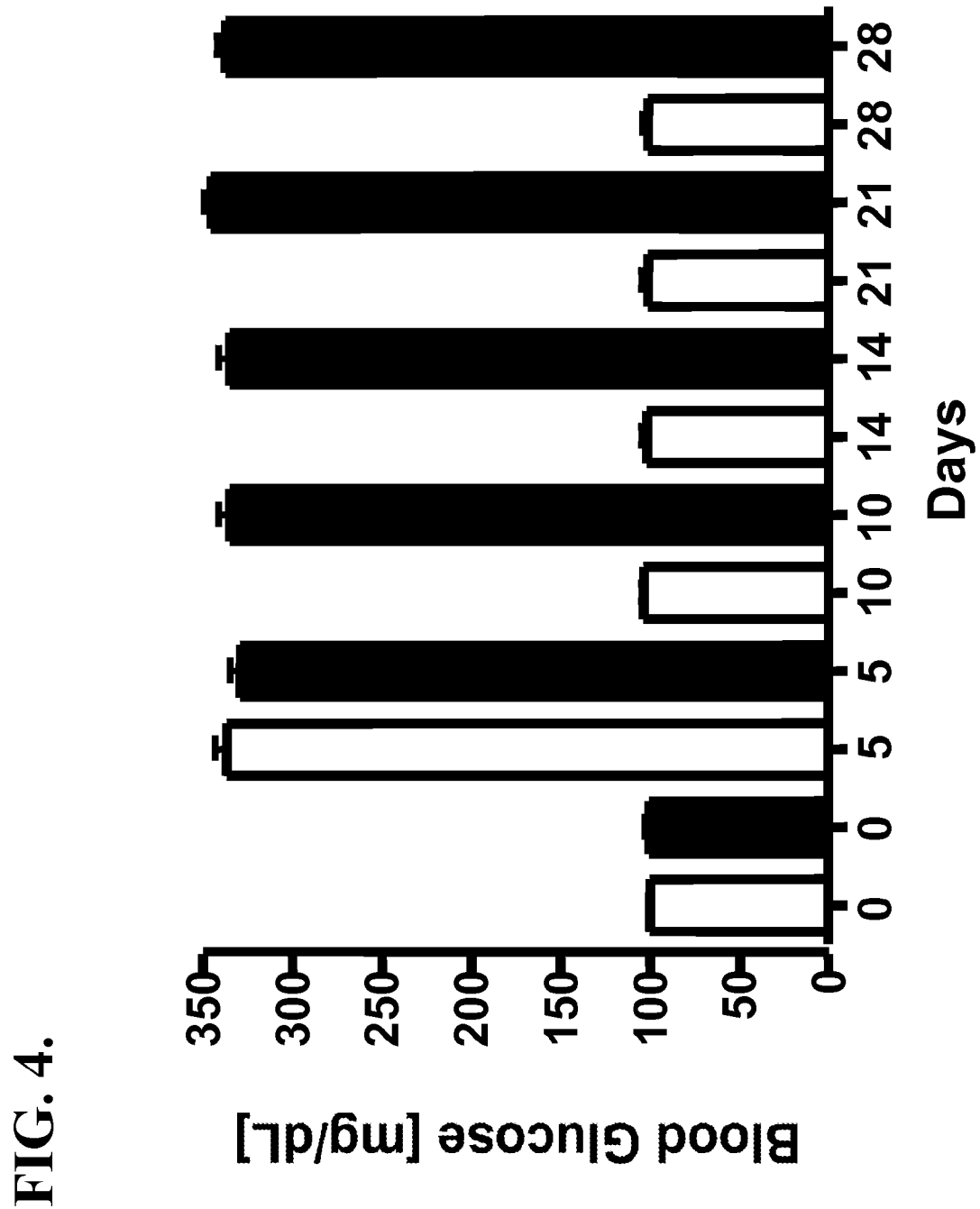
FIG. 4 depicts blood glucose levels in diabetic mice (black bars) versus diabetic mice treated with administration of β-MSC on day 5 (white bars). Animals were provided with a high glucose diet and blood glucose levels monitored.

A parallel experiment is depicted in FIG. 4. Therein, blood glucose levels of diabetic mice treated via the peritoneal cavity with $10^6$ β-MSC (white bars) are compared with untreated animals (black bars) during challenge with a high glucose diet. As can be seen, both groups of animals show high blood glucose levels before β-MSC treatment at day 5. However, by day 10, β-MSC treated animals show a return to normal blood glucose levels while those of the control group remain high. Increased mortality in the untreated groups was apparent by day 21. P<0.001 for the difference between treated and untreated groups at 10, 14, 21, and 28 days.

EXAMPLE 6

Figure 5:
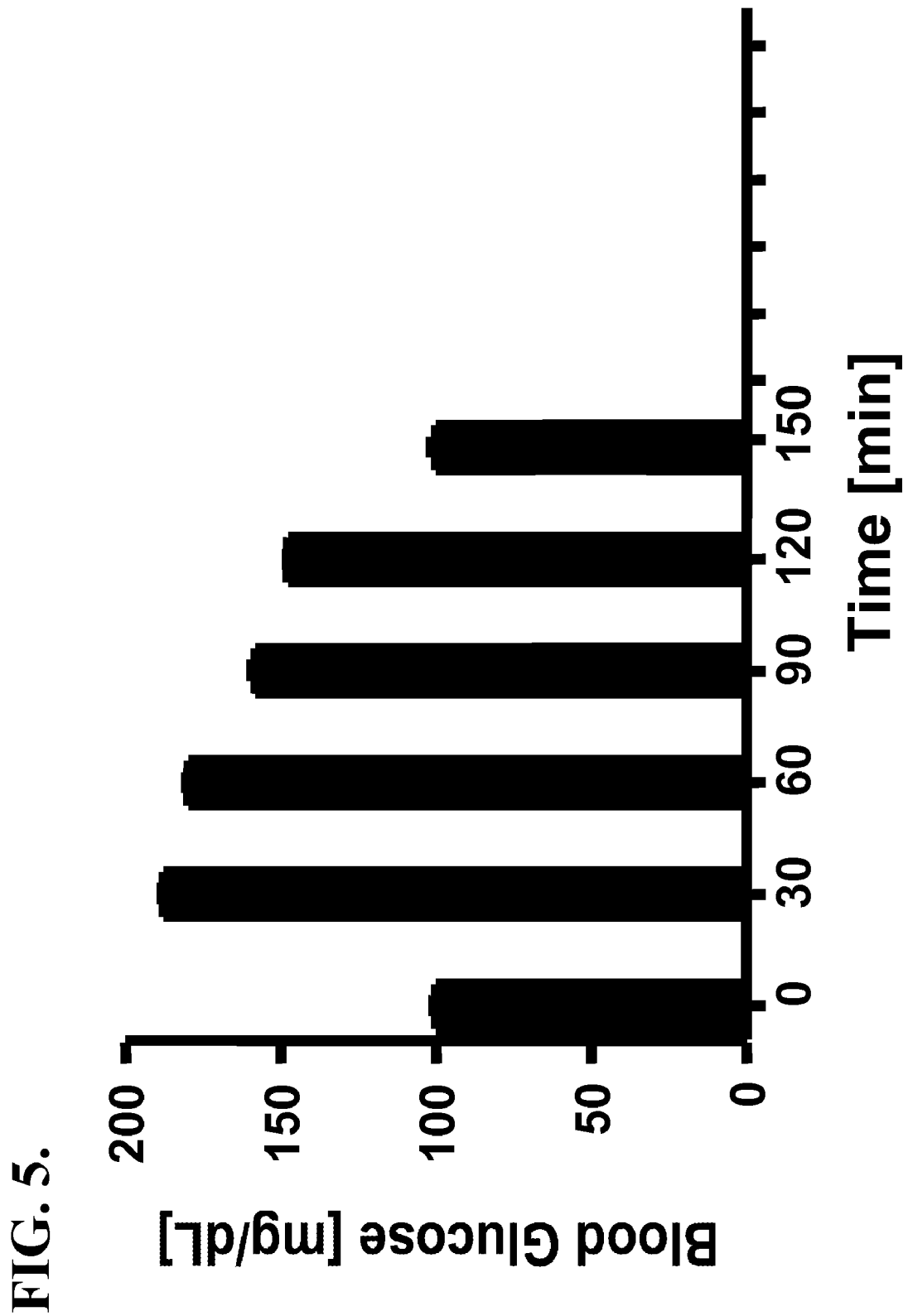
FIG. 5 depicts the results of a glucose tolerance test on diabetic mice that were treated via administration of β-MSC 21 days prior to the glucose tolerance test.

Intraperitoneal Glucose Tolerance Test of Diabetic Mice Treated with β-MSC Shows Normal Glucose Response A diabetic like state was induced in mice through the use of streptozotocin as is well known in the art. Animals were then treated with administration of β-MSC as described above and allowed to recover. After 21 days, animals were provided with an intraperitoneal glucose bolus and blood glucose levels were monitored every half hour. As is visible in FIG. 5, blood glucose levels returned to normal within 150 minutes which approximately corresponds to the glucose tolerance presented by normal animal.

EXAMPLE 7

Pharmaceutical Composition of β-MSC

β-MSC are prepared and isolated as provided in the above examples. The β-MSC are then grown and expanded in culture until a desired population is obtained. A pharmaceutical composition comprising β-MSC is then prepared by mixing β-MSC with a pharmaceutically acceptable excipient. A pharmaceutical composition comprising $10^6$ β-MSC in 0.2 ml PBS is prepared and may be frozen prior to administration. β-MSC are thus used in the manufacture of a medicament to treat diabetes mellitus

EXAMPLE 8

Treatment of Diabetes Mellitus in a Human Subject Via Administration of β-MSC

Human subjects having diabetes mellitus are administered a therapeutically effective amount of a pharmaceutical composition comprising β-MSC. In a first subject, β-MSC are administered into the portal vein with a catheter. In a second subject, β-MSC are placed into a porous, plastic capsule and the capsule is surgically placed into the anterior abdominal wall, only covered by the peritoneum. 21 days after implantation, both subjects respond normally to a glucose tolerance test. Blood C-peptide, insulin, and glucose levels are monitored top assess functionality of β-MSC cells over time. Subjects are effectively treated for diabetes mellitus.

EXAMPLE 9

Boosting of Treatment in a Human Subject Previously Administered β-MSC

Human subjects are administered β-MSC and thereafter show a reduction in glucose tolerance over a period of time. Blood C-peptide, insulin, and glucose levels are shifted to state more indicative of active diabetes mellitus. Additional β-MSC are administered as in Example 8. 21 days after implantation, subjects respond normally to a glucose tolerance test. Blood C-peptide, insulin, and glucose levels are monitored top assess functionality of β-MSC cells over time. Subjects are effectively treated for diabetes mellitus.

The foregoing Examples are directly relevant to subjects with diabetes mellitus, as they demonstrate that effective cell fusion between MSC and pancreatic β cells can be achieved in vitro. The resulting β-MSC secrete insulin in response to changes in ambient glucose concentration and proliferate while maintaining their phenotype and islet cell-like function. Because of the immunomodulating capacity of MSC, which is maintained after fusion with β cells, their survival in a recipient should be prolonged since immune injury is negligible, and since MSC secrete cytoprotective and vasculosupportive cytokines (HGF, IGF-I, VEGF). When β-MSC are administered to mice with DM, blood glucose control improves in correlation with reestablished endogenous insulin production.

All references, including publications, patents, and patent applications, cited herein are hereby incorporated by reference to the same extent as if each reference were individually and specifically indicated to be incorporated by reference and were set forth in its entirety herein.

Although the invention herein has been described in connection with preferred embodiments thereof, it will be appreciated by those skilled in the art that addition, modifications, substitutions, and deletions not specifically described may be made without departing from the spirit and scope of the invention as defined in the appended claims, and all embodiments that come within the meaning of the claims, either literally or by equivalence, are intended to be embraced therein.

REFERENCES

1a. Islam M Q et al.: Functional characterization of cell hybrids generated by induced cell fusion or primary porcine mesenchymal stem cells with an immortalized murine cell line. *Cell Tissue Res* 326:123-137, 2006.
1b. Islam M Q et al.: Generation of somatic cell hybrids for the production of biologically active factors that stimulate proliferation of other cells. *Cell Prolif* 40:91-105, 2007.
2. Ying Q-L et al.: Changing potency by spontaneous fusion. *Nature* 416:545-548, 2002 (neurons and ESC).
3a. Ogle B M et al.: Biological Implications of Cell Fusion. *Nature Review Mol Cell Biol* 6:567-75, 2005.
3b. Ogle B M et al.: Spontaneous fusion of cells between species yields transdifferentiation and retorviral transfer in vivo. *FASEB J* 18:584-50, 2004.
4a. Alvarez-Dolado M et al.: Fusion of bone-marrow-derived cells with Purkinje neurons, cardiomyocytes and hepatocytes. *Nature* 425:968-973, 2003.
4b. Wang X et al.: Cell fusion is the principal source of bone-marrow-derived hepatocytes. *Nature* 422:897-00, 2003.
4c. Vassilopoulos G et al.: Transplanted bone marrow regenerates liver by cell fusion. *Nature* 422:901-04, 2003.
5. Held P K et al.: In vivo genetic selection of renal proximal tubules. *Molec Therapy* 13:49-58, 2006.
6. Que J et al.: Generation of hybrid cell lines with endothelial potential, from spontaneous fusion of adult bone marrow cells with embryonic fibroblast feeder. *In Vitro Cell Dev Biol-Animal* 40:143-49, 2004.
7. Vassilopoulos G et al.: Cell fusion: an alternative to stem cell plasticity and its therapeutic implications. *Current Opinion in Genetics & Development* 13:480-85, 2003.
8. Rizvi A Z et al.: Bone marrow-derived cells fuse with normal and transformed intestinal stem cells. *PNAS* 103: 6321-5, 2006.

9. Spees J L et al.: Differentiation, cell fusion, and nuclear fusion during ex vivo repair of epithelium by human adult stem cells from bone marrow stroma. *PNAS* 100:2397-402, 2003.
10. Ambrosi D J et al.: Reprogramming mediated by stem cell fusion. *J Cell Molec Medicine* 9:320-30, 2005.
11. Cowan C A et al.: Nuclear reprogramming of somatic cells after fusion with human embryonic stem cells. *Science* 309:1369-73, 2005.
12. Shukhorukov V L et al.: Surviving high intensity field pulses: strategies for improving robustness and performance of electrotransfection and electrofusion. *J Membrane Biol* 206:187-201, 2005.
13. Li L H et al.: Electrofusion between heterogeneous-sized mammalian cells in a pellet: potential applications to drug delivery and hybridmoa formation. *Biophysical J* 71:479-86, 1996.
14. Lee R H at al.: Multipotent siromal cells from human marrow home to and promote repair of pancreatic islets and renal glomeruli in diabetic NOD/scid mice. PNAS 103: 17438-43, 2006.
15. Le Blanc K: Mesenchymal stromal cells: tissue repair and immune modulation. *Cytotherapy* 8:559-61, 2006.
16. Westenfedler C.: Stem-cell, precursor cell, or target cell-based treatment of multiorgan failure and renal dysfunction. U.S. Pat App. Publ. 2007017807A1
17. Togel F. et al. Adult bone marrow-derived stem cells for organ regeneration and repair. *Dev Dyn.* 2007 Aug. 8; [Epub ahead of print]

What is claimed is:

1. A cell wherein said cell is isolated and comprises a fusion of at least one pancreatic β cell and a Marrow Stromal Cell (MSC), wherein the nuclei of said pancreatic β cell and the MSC are not fused, and wherein the cell comprising a fusion of a pancreatic β cell and an MSC maintains at least two separate nuclei while proliferating in culture.

2. The cell of claim 1, wherein the MSC is isolated from an isogenic, allogenic, syngeneic, or xenogenic source relative to said pancreatic β cell.

3. The cell of claim 1, wherein said MSC is mammalian.

4. The cell of claim 1, wherein said pancreatic β cell is mammalian.

5. The cell of claim 1, wherein said cell produces increased insulin in response to glucose levels at or higher than 100 mg/dL.

6. The cell of claim 1 together with a pharmaceutically acceptable excipient.

7. A method of expressing insulin in a subject having diabetes mellitus, said method comprising delivering a therapeutically effective amount of a pancreatic β cell/Marrow Stromal Cell fusion (β-MSC) to a subject in need thereof, wherein the β-MSC comprise cells selected from the group consisting of autologous cells and allogenic cells, wherein the β-MSC maintain at least two nuclei while proliferating in culture; thereby producing insulin in the subject.

8. The method according to claim 7, wherein the diabetes mellitus is Type 1 Diabetes Mellitus (T1DM).

9. The method according to claim 7, wherein said β-MSC are transfected with a gene encoding Akt.

10. The method according to claim 8, wherein said β-MSC are stably transfected with a gene encoding Akt.

11. The method according to claim 7, wherein said β-MSC are infused with a catheter into the abdominal cavity or portal vein.

12. The method according to claim 7, wherein said β-MSC are placed into a biocompatible porous capsule that is surgically implanted.

13. The method according to claim 12, wherein said biocompatible porous capsule is surgically implanted just above the peritoneum of the anterior abdominal wall of a subject.

14. An isolated cell comprising at least one nucleus of a mammalian pancreatic β cell, and at least one nucleus of a mammalian Marrow Stromal Cell, the least one nuclei being maintained as separate structures, wherein the cell produces insulin in response to glucose levels at or higher than 100 mg/dl, and wherein the cell maintains the least one nucleus of the mammalian pancreatic β cell and least one nucleus of the mammalian Marrow Stromal Cell while proliferating in culture.

* * * * *